(12) United States Patent
Mason et al.

(10) Patent No.: US 10,390,691 B2
(45) Date of Patent: Aug. 27, 2019

(54) MEDICAL ACCESSORY HOLDER

(71) Applicant: Cantel (UK) Limited, Southend-on-Sea (GB)

(72) Inventors: David Mason, Southend on Sea (GB); Mark Jackson, Great Wakering (GB); Gary Spencer, Benfleet (GB)

(73) Assignee: Cantel (UK) Limited, Southend-on-Sea (GB)

( * ) Notice: Subject to any disclaimer, the term of this patent is extended or adjusted under 35 U.S.C. 154(b) by 281 days.

(21) Appl. No.: 15/387,163

(22) Filed: Dec. 21, 2016

(65) Prior Publication Data

US 2017/0181613 A1 Jun. 29, 2017

Related U.S. Application Data

(60) Provisional application No. 62/387,473, filed on Dec. 24, 2015.

(51) Int. Cl.
*B23Q 3/00* (2006.01)
*A61B 1/12* (2006.01)
(Continued)

(52) U.S. Cl.
CPC .......... *A61B 1/125* (2013.01); *A61B 1/00147* (2013.01); *A61B 1/123* (2013.01);
(Continued)

(58) Field of Classification Search
USPC ......... 269/287, 288; 206/363, 370, 561, 562
See application file for complete search history.

(56) References Cited

U.S. PATENT DOCUMENTS 3,013,656 A 12/1961 Murphy, Jr.
4,331,257 A 5/1982 Taschner
(Continued)

FOREIGN PATENT DOCUMENTS

DE 94181853 12/1994
DE 202005015801 U1 12/2005
(Continued)

OTHER PUBLICATIONS

International Search Report and Written Opinion of the International Searching Authority dated Apr. 18, 2017 of International PCT Application No. PCT/IB2016/001891 filed Dec. 21, 2016, entire document.

*Primary Examiner* — Joseph J Hail
*Assistant Examiner* — Shantese L McDonald
(74) *Attorney, Agent, or Firm* — Sorell, Lenna & Schmidt LLP; William D. Schmidt

(57) ABSTRACT

A medical accessory holder (10) is provided, for use during reprocessing and/or conditioning of medical equipment. The holder comprises a planar base portion (11). At least one recess (12, 13, 14) is provided in the planar base portion, and is adapted to receive a medical accessory (15, 16, 17) firmly engaged therein. The holder (10) further comprises retaining means (22) associated with the base portion (11) and adapted to engage therewith. Once engaged, the retaining means (22) cannot be disengaged, and the medical accessory (15, 16, 17) cannot be removed from the recess (12, 13, 14), without breaking the retaining means (22), thereby rendering the holder suitable only for single use. Attachment means (26) are further provided to enable the holder (10) to be secured to an article of medical equipment with which the medical accessory (15, 16, 17) is associated, during reprocessing thereof.

20 Claims, 2 Drawing Sheets

(51) Int. Cl.
  *A61B 50/20* (2016.01)
  *A61B 1/00* (2006.01)
  *A61B 90/70* (2016.01)
  *A61B 90/00* (2016.01)

(52) U.S. Cl.
  CPC .............. *A61B 50/20* (2016.02); *A61B 90/70* (2016.02); *A61B 2090/0814* (2016.02); *A61B 2090/701* (2016.02)

(56) References Cited

U.S. PATENT DOCUMENTS

| | | | |
|---|---|---|---|
| 4,711,352 A | 12/1987 | Williams et al. | |
| 5,031,768 A | 7/1991 | Fischer | |
| 5,096,114 A | 3/1992 | Higginbotham | |
| 5,163,557 A | 11/1992 | Sokolowski | |
| 5,234,124 A | 8/1993 | Buckner, III et al. | |
| 5,235,795 A | 8/1993 | DeBusk | |
| 5,372,787 A | 12/1994 | Ritter | |
| 5,482,067 A | 1/1996 | Wittrock et al. | |
| 5,993,754 A | 11/1999 | Lemmen et al. | |
| 6,910,581 B2 * | 6/2005 | McMichael | A61B 50/30 206/370 |
| 8,789,695 B2 | 7/2014 | Mason | |
| 8,925,723 B2 * | 1/2015 | Folchini | A61M 5/002 206/364 |
| 2003/0080571 A1 | 5/2003 | Schainholz et al. | |
| 2004/0238014 A1 | 12/2004 | Halstead et al. | |
| 2005/0139599 A1 | 6/2005 | Schainholz et al. | |
| 2005/0161355 A1 | 7/2005 | Matthis et al. | |
| 2006/0266666 A1 | 11/2006 | Bettenhausen et al. | |
| 2007/0144926 A1 | 6/2007 | Bettenhausen et al. | |
| 2010/0158751 A1 | 6/2010 | Friderich et al. | |
| 2011/0083983 A1 * | 4/2011 | Walters | A61B 46/23 206/370 |
| 2015/0150630 A1 * | 6/2015 | Lotosky-Compton | A61B 50/20 206/370 |
| 2016/0058518 A1 * | 3/2016 | Mason | A61L 2/186 206/363 |

FOREIGN PATENT DOCUMENTS

| | | |
|---|---|---|
| DE | 202010005089 | 7/2010 |
| DE | 102009011528 A1 | 8/2010 |
| EP | 0307173 A1 | 3/1989 |
| EP | 0808782 A1 | 11/1997 |
| FR | 2543110 A1 | 9/1984 |
| GB | 2281359 A | 5/1993 |
| GB | 2475948 A | 6/2011 |
| GB | 2485011 A | 5/2012 |
| GB | 2485818 A | 5/2012 |
| GB | 2513643 A | 11/2014 |
| JP | 2003175003 A | 6/2003 |
| NL | 2005411 C | 3/2012 |
| WO | 2004018305 A2 | 3/2004 |
| WO | 2005053597 A2 | 6/2005 |
| WO | 2006127230 A2 | 11/2006 |

\* cited by examiner

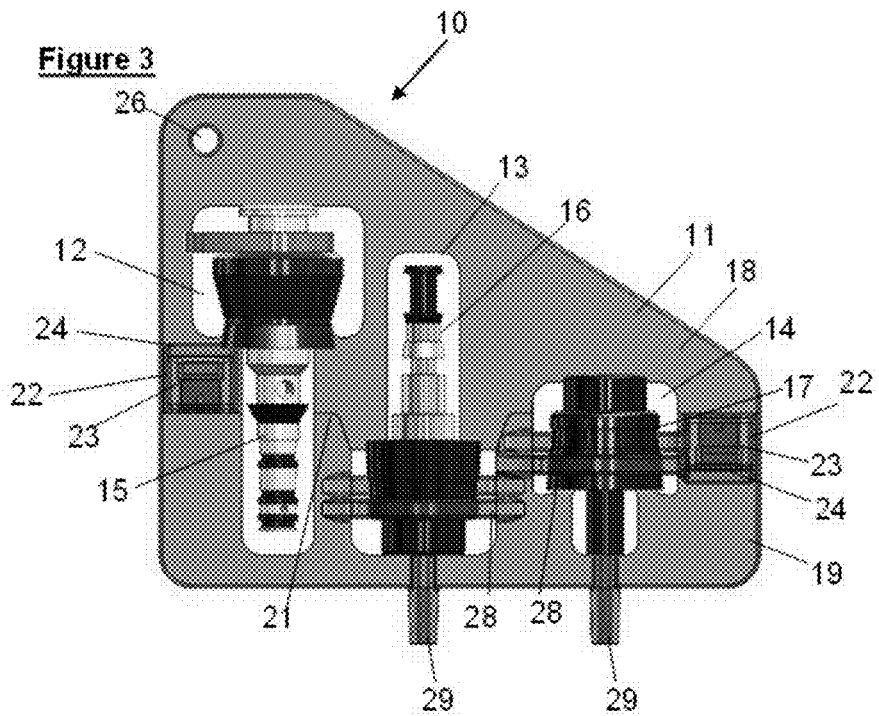
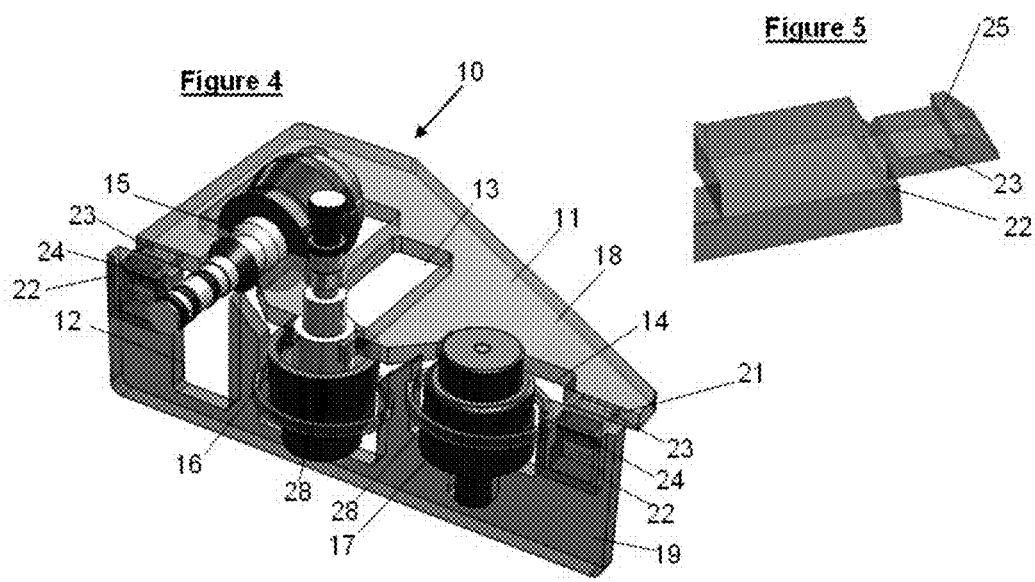

MEDICAL ACCESSORY HOLDER

BACKGROUND

This application relates to a medical accessory holder for use in reprocessing and conditioning. In particular, it relates to a single-use holder for retaining the valves of a flexible medical endoscope during reprocessing and conditioning. The term "reprocessing" is used herein to refer to cleaning and high level disinfection of medical equipment following its use on a patient. The term "conditioning" is used herein to refer to maintaining medical equipment at the disinfection level achieved during the previous reprocessing procedure.

Following use on a patient, medical equipment must be reprocessed to, and maintained at, a high level of disinfection. This is a particular necessity for medical equipment utilized in invasive procedures, such as flexible medical endoscopes, with which the present application is primarily concerned.

Flexible medical endoscopes typically comprise a number of channels for the delivery of air, water, other fluids, or devices. These may be utilized for the delivery of such fluids to the interior of a patient where this is required during a medical procedure, for the removal of fluid (by suction) from the interior of a patient, or for cleaning the viewing window or lens of the endoscope. Operation of these channels is typically controlled by a number of valves (sometimes referred to as pistons or adaptors) operated remotely by the practitioner carrying out the endoscopy procedure.

During reprocessing of a flexible medical endoscope following its use on a patient, the valves must be removed, in order that each of the channels can be thoroughly cleaned and disinfected. The valves themselves must also be subjected to the same reprocessing regime to bring them to a state of high level disinfection. Typically, reprocessing of flexible medical endoscopes and associated accessories such as the valves, is now carried out on an automated basis using a specially designed reprocessing machine, known as an Automated Endoscope Reprocessor (AER) machine or an Endoscope Washer Disinfector (EWD). In a busy hospital endoscopy department, this can cause problems, since the valves specific to a particular endoscope can easily become separated from that endoscope during reprocessing. This can lead to cross-contamination if a set of valves associated with one endoscope are accidentally inserted into a different endoscope.

In addition, the valves are spring activated and as a result, not all surfaces are exposed during reprocessing, which may present a cross-infection risk.

Accessories such as endoscope valves are often placed into auxiliary containers, before being placed into the AER machine along with the endoscope. Ideally, such auxiliary containers should only be used once, and then disposed of, in order to eliminate them as a possible source of cross-contamination between different endoscopes which may be reprocessed using the same machine. Indeed, concerns regarding the levels of disinfection to which endoscopes and their associated accessories are processed, and at which they are maintained, have led to increasingly strict guidelines regulating the manner in which reprocessing is carried out. For example, the British Society of Gastroenterology (BSG) Guidelines for Decontamination of Equipment for Gastrointestinal Endoscopy stipulate that such auxiliary containers must be single use items, and must be disposed of after use. In practice however, this ideal is not always achieved, in particular since it is often not possible to tell whether a container has been used previously.

The Applicant's own Patent Publication No. GB 2,485,818 discloses a container for housing a medical accessory during reprocessing. The container has a closure mechanism adapted such that once closed it cannot be re-opened without the container breaking. The container is thus rendered suitable only for single use.

The Applicant's own Patent Publication No. GB 2,513,643 discloses a holder for retaining a medical accessory during reprocessing. The holder has a retaining mechanism adapted such that once engaged the medical accessory cannot be removed without the holder breaking. The holder is thus rendered suitable only for single use.

The Applicant's own Patent Publication No. GB 2,483,741 discloses a method and apparatus, referred to as a conditioning station, for conditioning a flexible medical endoscope by delivering a conditioning agent to the internal channels of the endoscope.

SUMMARY

The present application seeks to improve upon the devices of GB 2,485,818, which is described in U.S. Patent Publication No. 2013/0233746 A1, herein incorporated by reference and GB 2,513,643, which is described in PCT Publication No. 2014/177838 A1, herein incorporated by reference, by providing a single use medical accessory holder for retaining the valves of a flexible medical endoscope during both reprocessing in an AER or EWD machine, and conditioning, and which is adapted for use with the method and apparatus of GB 2,482,741, which is also described in U.S. Patent Publication No. 2013/0205720 A1, herein incorporated by reference. Although the medical accessory holder of the present application has been developed with endoscope valves in mind, it is envisaged that the holder may be adapted for use with substantially all kinds of medical accessory, and the disclosure of the application herein should be construed accordingly.

According to the present application there is provided a medical accessory holder for use during reprocessing and/or conditioning of medical equipment, said holder comprising: a planar base portion; at least one recess provided in the planar base portion, each said recess being adapted to receive a medical accessory therein, such that said medical accessory is firmly engaged in said recess; retaining means associated with the base portion and adapted to engage therewith such that, once engaged, the retaining means cannot be disengaged, and said medical accessory cannot be removed from said recess, without breaking the retaining means, thereby rendering said holder suitable only for single use; and attachment means adapted to enable said holder to be secured to an article of medical equipment with which said medical accessory is associated, during reprocessing thereof.

The medical accessory holder of the present application is intended for use during the reprocessing and conditioning of medical equipment. In particular, it is adapted to be reprocessed in a medical equipment reprocessing or conditioning machine—such as an automated endoscope reprocessing (AER/EWD) machine in the preferred case where the medical accessory is a component of a flexible medical endoscope. Most preferably, the medical accessory is a flexible medical endoscope valve, and said at least one recess is adapted to receive a said flexible medical endoscope valve.

The medical accessory holder of the present application preferably comprises two or more, and most preferably three recesses, each adapted to receive a flexible medical endoscope valve. In preferred embodiments, each recess will be specifically adapted to accommodate a different shape and configuration of flexible medical endoscope valve, e.g. air/water and suction valves, and air/water cleaning adaptors. The holder is thus preferably adapted to hold all valves associated with a specific endoscope.

At least one, and preferably each, recess is preferably further provided with one or more protrusions adapted to engage with a said flexible medical endoscope valve located in said recess, and to maintain said valve in a compressed (open) condition. This facilitates reprocessing or conditioning of the internal parts of said valve. To that end, the holder preferably further comprises one or more connectors, each in communication with a said recess, and adapted to deliver fluid to a said medical accessory. Each said connector is preferably adapted to deliver reprocessing or conditioning fluid to internal channels of a said flexible medical endoscope valve. This adaptation further enables the medical accessory holder to be utilized in combination with a conditioning station, such as that described in liquid condition agent of the Applicant's GB 2,483,741. Said connector may thus be adapted to receive cleaning and/or disinfecting fluid from said conditioning station.

Each recess is preferably further adapted to hold and retain a flexible medical endoscope valve in an orientation aligned with the plane of the base portion. To that end, at least one, and preferably each, recess is preferably provided with stabilizing means arranged so as maintain the orientation of a flexible medical endoscope valve in said recess. The stabilizing means may preferably comprise a stabilizing bar or ring.

The attachment means is preferably adapted to enable said holder to be secured to a flexible medical endoscope—and in particular, the specific flexible medical endoscope with which the component is associated—during reprocessing thereof. In a currently preferred embodiment of the present application, the attachment means comprises an aperture formed in the planar base portion and adapted to receive a tie element to secure said holder to an endoscope.

In a preferred embodiment of the present application, the base portion is formed from two or more interconnecting sections, and the retaining means is adapted to lock said interconnecting sections together.

In this preferred embodiment, the base portion preferably comprises a first section, and a second section adapted to engage therewith. Said first and second sections may be connected via a hinge, or may be separate components. The retaining means preferably comprises at least one locking clip mechanism, said mechanism preferably comprising a male component provided on one of said first and second sections, and a female component provided on the other of said first and second sections. Once engaged, the male component cannot be disengaged from the female component without breaking the locking clip mechanism, thus rendering the holder suitable only for single use.

In an alternative embodiment of the present application, the retaining means comprises: a retaining strap adapted to extend over each recess, thereby to retain each said medical accessory therein; and one or more fixing points provided on the base portion, with which said strap is adapted to engage. The retaining strap may be connected to the base portion via a live hinge.

Each fixing point may comprise an upstanding peg, with the retaining strap being provided with one or more holes each adapted to engage with a corresponding peg, such that once engaged, the peg cannot be disengaged from the hole without breaking the retaining means, thus rendering the holder suitable only for single use. In particular, the peg may be adapted to break upon disengagement of the retaining strap.

The retaining strap may preferably be further adapted so as to constitute the attachment means adapted to enable said holder to be secured to an article of medical equipment with which said medical accessory is associated.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 3 shows a front view of the medical accessory holder of FIGS. 1 and 2, in use with flexible medical endoscope valves mounted therein;

FIG. 4 shows a perspective front view of the medical accessory holder of FIGS. 1 to 3, in an open condition after use in order to allow retrieval of the flexible medical endoscope valves; and FIG. 5 shows an enlarged detail of the retaining means of the medical accessory holder of FIGS. 1 to 4.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "a recess" includes one, two, three or more recesses.

Figure 1:
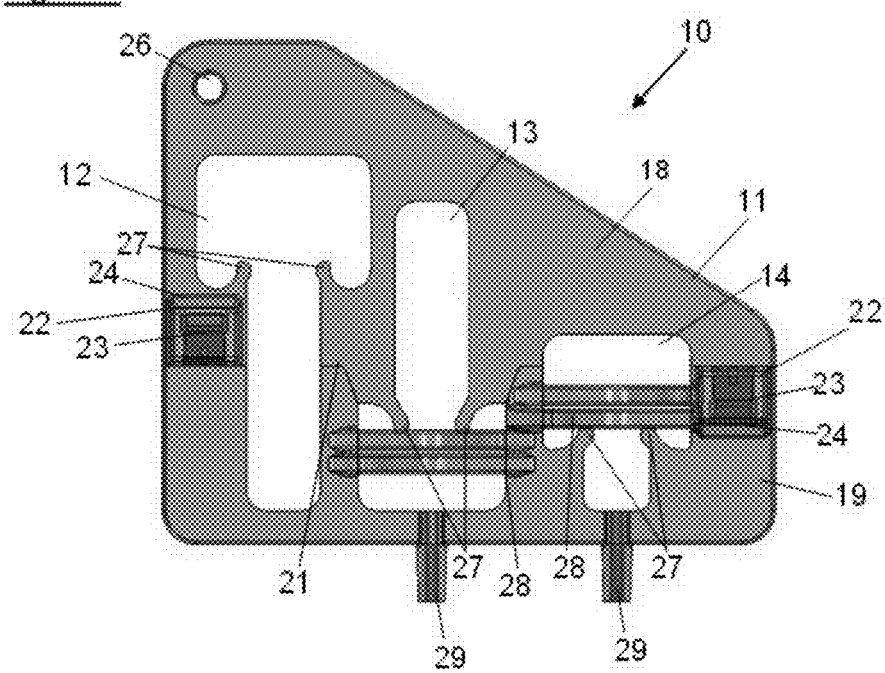
FIG. 1 shows a front view of a medical accessory holder according to a preferred embodiment of the present application.
Figure 2:
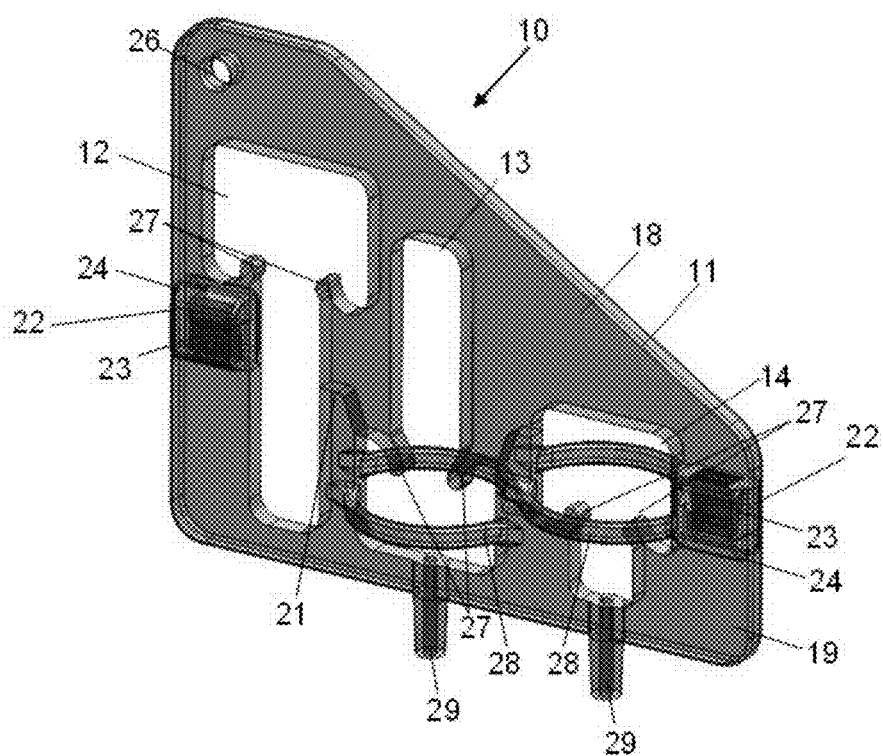
FIG. 2 shows a perspective front view of the medical accessory holder of FIG. 1.

Referring first to FIGS. 1 and 2, there is shown a medical accessory holder, generally indicated 10, according to a preferred embodiment of the present application. The holder 10 comprises a planar base portion 11, with recesses 12, 13, 14 formed therein. As can best be seen in FIG. 3, each recess 12, 13, 14 is differently shaped and dimensioned so as to accommodate a different shape and configuration of flexible medical endoscope valve 15, 16, 17 (for example air/water suction valves) therein.

Referring again to FIGS. 1 and 2, the planar base portion 11 and air water channel cleaning adaptor is formed by interconnecting upper and lower sections 18, 19. A boundary 21 is visible between the upper and lower sections 18, 19. As can be seen in FIG. 4, the upper section 18 is removably mountable on the lower section 19. This may either be achieved by forming a hinge in the boundary 21, or by forming the upper and lower sections 18, 19 as separate, but interconnecting, components.

Referring again to FIGS. 1 and 2, the base portion 11 is provided with retaining means, which in this preferred embodiment of medical accessory holder 10, take the form of a locking clip mechanism 22. One such mechanism 22 is provided adjacent each end of the boundary 21 between the upper and lower sections 18, 19 of the base portion 11. Each locking clip mechanism 22 comprises a male component 23 provided on one of the upper section 18 and the lower section 19, and a female component 24 provided on the other section 18, 19.

The locking clip mechanism 22 is adapted to operate such that the male component 23 cannot be disengaged from the female component 24 without breaking the locking clip mechanism 22. As can be seen from FIG. 5, this is achieved by the provision of a protruding latch 25 on the male component 23, said latch 25 being adapted to engage with a corresponding element in the female component 24. In this way, the medical accessory holder 10 is adapted such that, once the upper section 18 and lower section 19 are interconnected with one another, they cannot be disengaged without breaking the locking clip mechanism 22, and thus effectively breaking the holder itself. Since, as shown in FIG. 4, the upper section 18 and the lower section 19 must be disengaged from one another in order to retrieve the valves 15, 16, 17 from the recesses 12, 13, 14, this renders the holder 10 suitable only for single use.

Referring once more to FIGS. 1 and 2, it can be seen that the base portion 11 is further provided with attachment means in the form of an aperture 26. The aperture 26 is adapted to receive a tie element (not shown) thereby to secure the holder 10 to an endoscope with which the valves 15, 16, 17 are associated, during reprocessing of said endoscope.

As can also be seen, each recess 12, 13, 14 is provided with a pair of opposed protrusions 27. These protrusions 27 serve both to assist with retaining the valves 15, 16, 17 in an orientation aligned with the plane of the base portion 11, and also to retain the valves 15, 16, 17 in a compressed (open) condition such that internal parts thereof can be exposed to cleaning fluid during reprocessing and conditioning.

Further assistance in the retention of valves 16, 17 in an orientation aligned with the plane of the base portion 11, is afforded by stabilizing rings 28 provided on recesses 13, 14. As can be seen from FIG. 3, the stabilizing rings 28 engage with valves 16, 17 thereby to retain them in the desired orientation.

As can also be seen in FIG. 3, recesses 13, 14 are further provided with connectors 29 adapted to deliver fluid to the internal parts of valves 16, 17, which are held in a compressed (open) condition by the action of the protrusions 27. The connectors may be adapted to receive liquid conditioning agent fluid from a conditioning station (not shown).

In use, the valves 15, 16, 17 of a flexible medical endoscope are inserted into the recesses 12, 13, 14, with the medical accessory holder 10 in an open position as shown in FIG. 4. The upper section 18 and lower section 19 are then brought into alignment, and the locking clip mechanisms 22 engaged, thus locking the holder 10 in a closed position as shown in FIG. 3. After reprocessing and conditioning, the holder 10 must be returned to the open position shown in FIG. 4 in order to retrieve the valves 15, 16, 17. However, this open position can now only be regained by breaking the locking clip mechanisms 22, and thus the holder 10. The holder 10 can therefore not be returned again to the closed position shown in FIG. 3, and so is suitable only for single use.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A medical accessory holder for use during reprocessing and/or conditioning of medical equipment, said holder comprising: a planar base portion having an upper section and a lower section wherein the upper section is removably mountable on the lower section; by an interconnecting means; at least one recess provided in the planar base portion, each said recess being adapted to receive a medical accessory therein, such that said medical accessory is firmly engaged in said recess retaining means associated with the base portion and adapted to engage therewith such that, once engaged, the retaining means cannot be disengaged, and said medical accessory cannot be removed from said recess, without breaking the retaining means, thereby rendering said holder suitable only for single use; and attachment means adapted to enable said holder to be secured to an article of medical equipment with which said medical accessory is associated, during reprocessing thereof.

2. A medical accessory holder according to claim 1, wherein the medical accessory is a component of a flexible medical endoscope.

3. A medical accessory holder according to claim 2, wherein the medical accessory is a flexible medical endoscope valve, and said recess is adapted to receive a said flexible medical endoscope valve.

4. A medical accessory holder according to claim 3, comprising two or more recesses, each adapted to receive a flexible medical endoscope valve.

5. A medical accessory holder according to claim 3, wherein each recess is adapted to hold a flexible medical endoscope valve in an orientation aligned with the plane of the base portion.

6. A medical accessory holder according to claim 5, wherein at least one recess is provided with stabilizing means arranged so as maintain said orientation of said flexible medical endoscope valve in said recess.

7. A medical accessory holder according to claim 6, wherein said stabilizing means comprises a stabilizing bar or ring.

8. A medical accessory holder according to claim 3, wherein at least one recess is further provided with one or more protrusions adapted to engage with a said flexible medical endoscope valve located in said recess, and to maintain said valve in a compressed (open) condition.

9. A medical accessory holder according to claim 3, further comprising one or more connectors, each in communication with a said recess, and adapted to deliver fluid to a said medical accessory.

10. A medical accessory holder according to claim 9, wherein each connector is adapted to deliver reprocessing or conditioning fluid to internal channels of a said flexible medical endoscope valve.

11. A medical accessory holder according to claim 9, wherein the connector is adapted to receive reprocessing or conditioning fluid from a conditioning station.

12. A medical accessory holder according to claim 1, wherein the base portion is formed from two or more interconnecting sections, and wherein the retaining means is adapted to lock said interconnecting sections together.

13. A medical accessory holder according to claim 12, wherein the base portion comprises a first section, and a second section adapted to engage therewith.

14. A medical accessory holder according to claim 13, wherein said first and second sections are connected via a hinge.

15. A medical accessory holder according to claim 13, wherein said retaining means comprises at least one locking clip mechanism.

16. A medical accessory holder according to claim 15, wherein said at least one locking clip mechanism comprises a male component provided on one of said first and second sections, and a female component provided on the other of said first and second sections.

17. A medical accessory holder according to claim 16, wherein once engaged, said male component cannot be disengaged from said female component without breaking the locking clip mechanism.

18. A medical accessory holder according to claim 1, wherein the upper section is transverse to the lower section.

19. A medical accessory holder according to claim 1, wherein the holder comprises a visible boundary between the upper and the lower section such that the upper section and the lower section interconnects at and around the boundary.

20. A medical accessory holder according to claim 1, wherein the interconnecting means is a clip or hinge.

* * * * *